United States Patent [19]
Levinson et al.

[11] Patent Number: 5,916,155
[45] Date of Patent: Jun. 29, 1999

[54] FETAL SENSOR WITH SECURING BALLOONS REMOTE FROM OPTICS

[75] Inventors: Mitchell Levinson, Pleasanton; Paul D. Mannheimer, Danville; James R. Casciani, Cupertino, all of Calif.

[73] Assignee: Nellcor Puritan Bennett Incorporated, Pleasanton, Calif.

[21] Appl. No.: 08/931,922

[22] Filed: Sep. 17, 1997

Related U.S. Application Data

[63] Continuation of application No. 08/688,492, Jul. 30, 1996, abandoned.

[51] Int. Cl.⁶ ............................................... A61B 5/00
[52] U.S. Cl. ........................... 600/338; 600/376; 600/339
[58] Field of Search ..................... 600/338, 376, 600/310, 322, 323–327, 339–341, 473, 476, 588, 407, 453, 454, 504, 505; 606/7, 13, 14

[56] References Cited

U.S. PATENT DOCUMENTS 5,377,675  1/1995  Ruskewicz et al. ................... 600/338

FOREIGN PATENT DOCUMENTS

91/07910  6/1913  WIPO .

*Primary Examiner*—John P. Leubecker
*Assistant Examiner*—Bryan K. Yarnell
*Attorney, Agent, or Firm*—Townsend and Townsend and Crew LLP

[57] ABSTRACT

An oximeter sensor with an expandable element for positioning the sensor against the fetus. The expandable element is positioned to be removed from at least one of the emitter and detector so that the portion of the sensor adjacent the emitter or detector is not pressed unduly by the expandable element to exsanguinate the tissue. A constant pressure differential between a pressure of the expandable element and an amniotic pressure may be maintained.

17 Claims, 5 Drawing Sheets

FETAL SENSOR WITH SECURING BALLOONS REMOTE FROM OPTICS

This is a Continuation of application Ser. No. 08/688,492, filed Jul. 30, 1996, now abandoned, the disclosure of which is incorporated by reference.

BACKGROUND OF THE INVENTION

The present invention relates to a non-invasive pulse oximetry fetal intrauterine sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate the amount of blood constituent being measured.

The light passed through the tissue is selected to be of one or more wavelengths that are absorbed by the blood in an amount representative of the amount of the blood constituent present in the blood. The amount of transmitted light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Known non-invasive sensors include devices that are secured to a portion of the body, such as a finger, ear or the scalp. In animals and humans, the tissue of these body portions is perfused with blood and the tissue surface is readily accessible to the sensor.

It is desirable that photoelectric pulse oximetry also be useful for monitoring the blood flow characteristics and constituents of a fetus. For example, monitoring fetal oxygen levels provides an effective way to detect and provide indications for treating hypoxia in the fetus during labor. However, known sensors adapted for use on infants or adults are not suited for intrauterine placement.

The environment in which the non-invasive intrauterine sensor must operate is fluid-filled (e.g., by amniotic fluid) and is only accessible through the restricted opening of the cervix. Visual inspection of the fetus and the sensor is likewise restricted. Moreover, the operating environment presents certain variants that interfere with detection of the fetal blood flow characteristics using known pulse oximetry techniques. For example, the presence of the waxy vernix caseosa, hair, mucus, blood and dead tissue cells on top of the fetal tissue surface against which the sensor is to be positioned create a problem in establishing contact between the optical components of the sensor and the surface of blood-perfused tissue. Detection of fetal blood flow characteristics by pulse oximetry is particularly complicated by the relatively low perfusion and low oxygen saturation of blood in fetal tissue. These environmental factors prevent known sensors from providing reliable information needed to calculate fetal blood characteristics.

It is known that positive attachment of a sensor to the tissue surface improves the quality of the photoelectric signal provided by the sensor. Positive attachment to a human's tissue may be obtained by vacuum, adhesives, tapes or devices such as clothespin-type clips. However, fetal tissue is relatively moist and there is limited access to the tissue surface. Consequently, conventional adhesives or tapes or clips are not adapted for intrauterine use.

U.S. Pat. No. 5,247,932 shows a bladder between the fetus and the uterine wall which presses the active face of the sensor against the fetus' skin. U.S. Pat. No. 5,377,675 discloses a sensor using a fulcrum to bias the sensor against the fetus.

A disadvantage of pressing a sensor too hard against a fetus' head by use of balloons or other mechanisms is that the tissue beneath the sensor becomes exsanguinated. Thus, with less blood in the tissue immediately beneath the sensor, accurate readings are more difficult. Accordingly, it is desirable to provide a fetal sensor which minimizes this exsanguination.

SUMMARY OF THE INVENTION

The present invention provides a sensor with a balloon or an equivalent expandable element for exerting pressure for accomplishing one or both of two purposes: (1) holding the sensor in place against the fetus, and (2) maintaining sensor position relative to the fetus' face during use. The balloons are positioned to be remote from the sensor element so that the fetal tissue adjacent the sensor element is not significantly compressed by the force of the balloon to exsanguinate the tissue. Alternate expandable elements include springs and foam.

In a preferred embodiment, a fetal pulse oximetry sensor having an emitter and detector in a sensor housing is provided. The balloon is either attached to the leading edge of the sensor housing beyond the optics (the distal end), or behind the sensor housing adjacent the cable jacket (the proximal end). In one embodiment, the balloon is at least one-quarter inch, more preferably one inch, in a lateral direction away from the sensor optics. Thus, the balloon will compress the skin at a position removed from the sensor optics.

Alternately, the balloon may be located on or near one, but not both, of the emitter and detector regions of the sensor, such that the force exerted by the balloon does not affect the tissues immediately beneath both of the regions. For example, the balloon may be located directly above the emitter region, while a detector located at a spaced apart location is at least one quarter of an inch away from the nearest edge of the balloon. In this way, all of the detected light will travel through at least some non-exsanguinated tissues.

In one embodiment, the balloon provides a constant pressure, to provide a constant force holding the sensor against the fetus. Saline solution may be used to fill the balloon.

For a further understanding of the nature and advantages of the invention, reference should be made to the following description taken in conjunction with the accompanying drawings.

DESCRIPTION OF THE PREFERRED EMBODIMENTS

Figure 1:
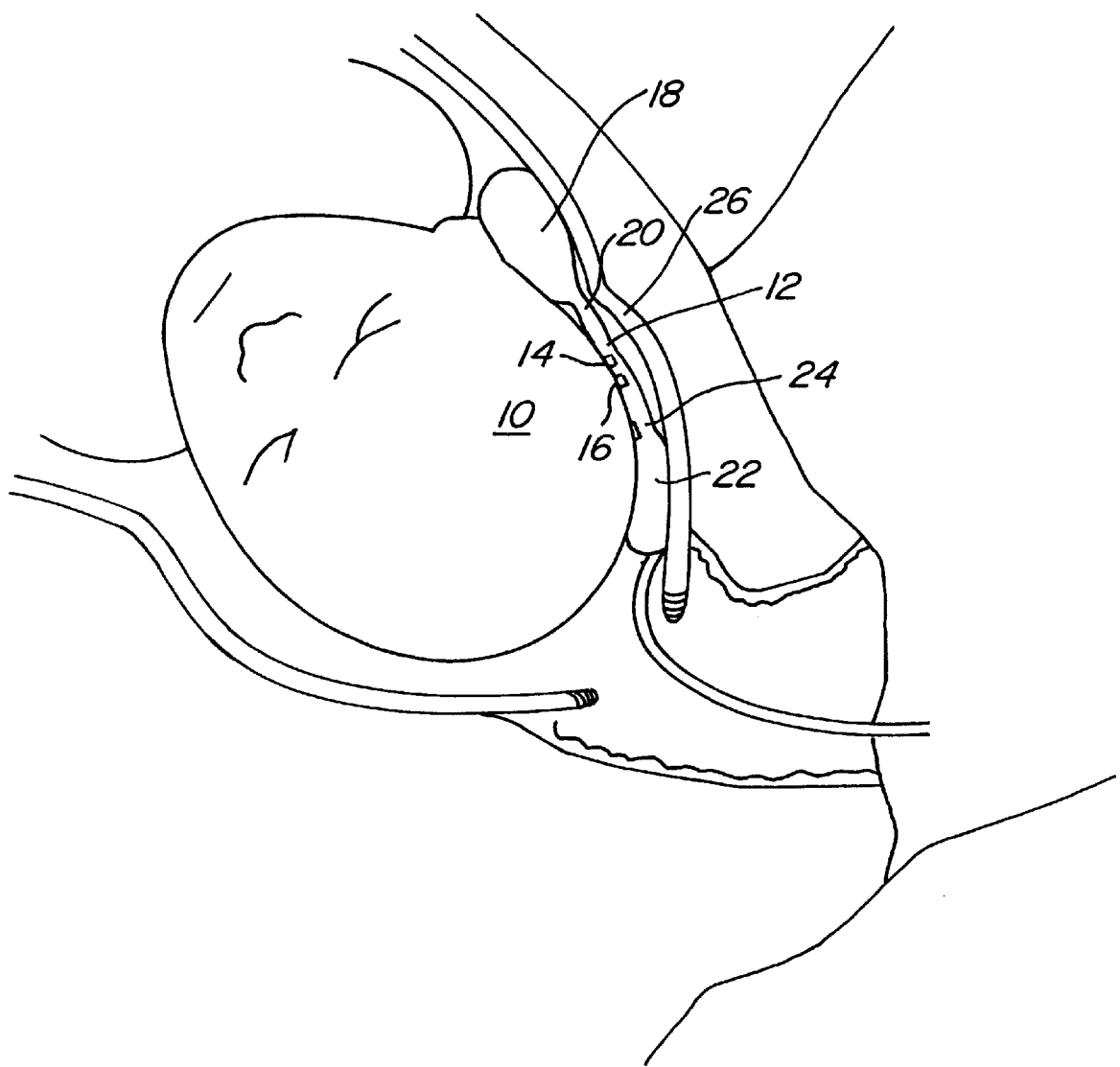
FIG. 1 is a diagram of an embodiment of the invention using two balloons.

FIG. 1 illustrates a first embodiment of the invention in place against the head of a fetus 10. The sensor includes a sensor housing 12 with an emitter 14 and a detector 16. A first balloon 18 is attached to a leading edge 20 of the sensor body, while a second balloon 22 is attached to a trailing edge 24 of the sensor body.

As can be seen, the balloons do not apply pressure to the portion of the fetus 10 below the emitter and detector. Rather, they apply pressure at positions proximal and distal to the sensor optics, thus exsanguinating the tissue at a position where it will not substantially affect the accuracy of the measurement. In the prior art, on the other hand, a balloon is typically attached immediately behind the sensor optics in order to force them against the fetus' head. The inventors have discovered, however, that this function can be provided with the balloons removed as shown.

In one embodiment, the balloon need not force the sensor body against the fetus' head, since a uterine wall 26 will do this. Rather, the balloons can be used to prevent the sensor from moving farther into the uterus or sliding out of the uterus to maintain it in position at the optimal position. Alternately, the balloons can also provide a force at the edge of the sensor which does press the entire sensor against the fetus' head, but with less intense pressure at the position of the sensor optics.

Figure 2:
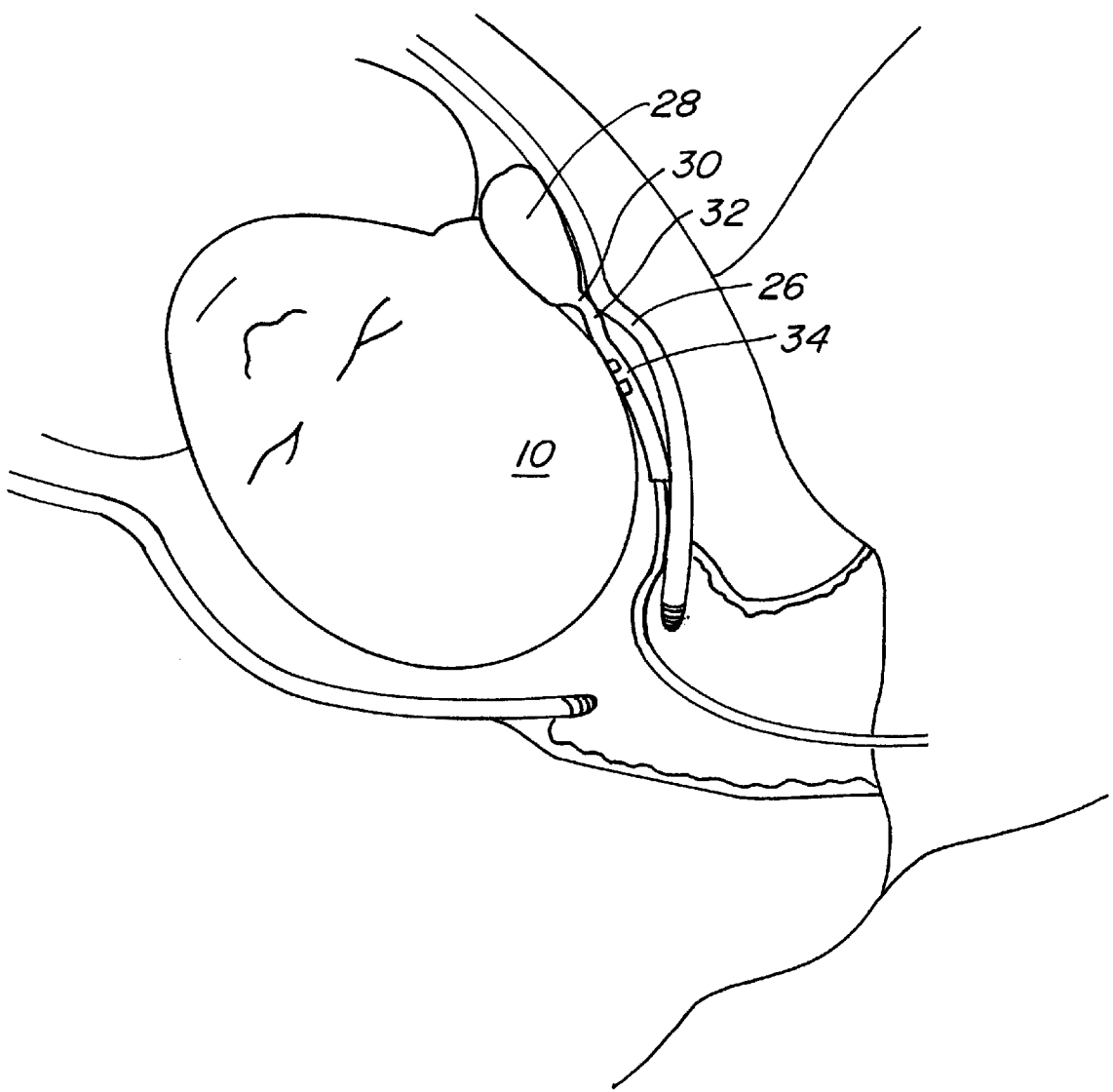
FIG. 2 is a diagram of an embodiment of the invention using a balloon beyond the leading edge of the sensor.

FIG. 2 shows an alternate embodiment of the present invention in which a balloon 28 is attached to a leading edge 30 of the sensor distal to the optics. In this instance, the leading edge has a fulcrum-shape, with a bend point 32 of the fulcrum contacting the uterine wall and forcing the body 34 of the sensor against the fetus 10. The balloon could also be combined with other mechanisms for biasing the body of the fetus against the head with the balloon either serving a partial biasing function, or solely serving the function of preventing the sensor housing from sliding farther into or out of the uterus.

Figure 3:
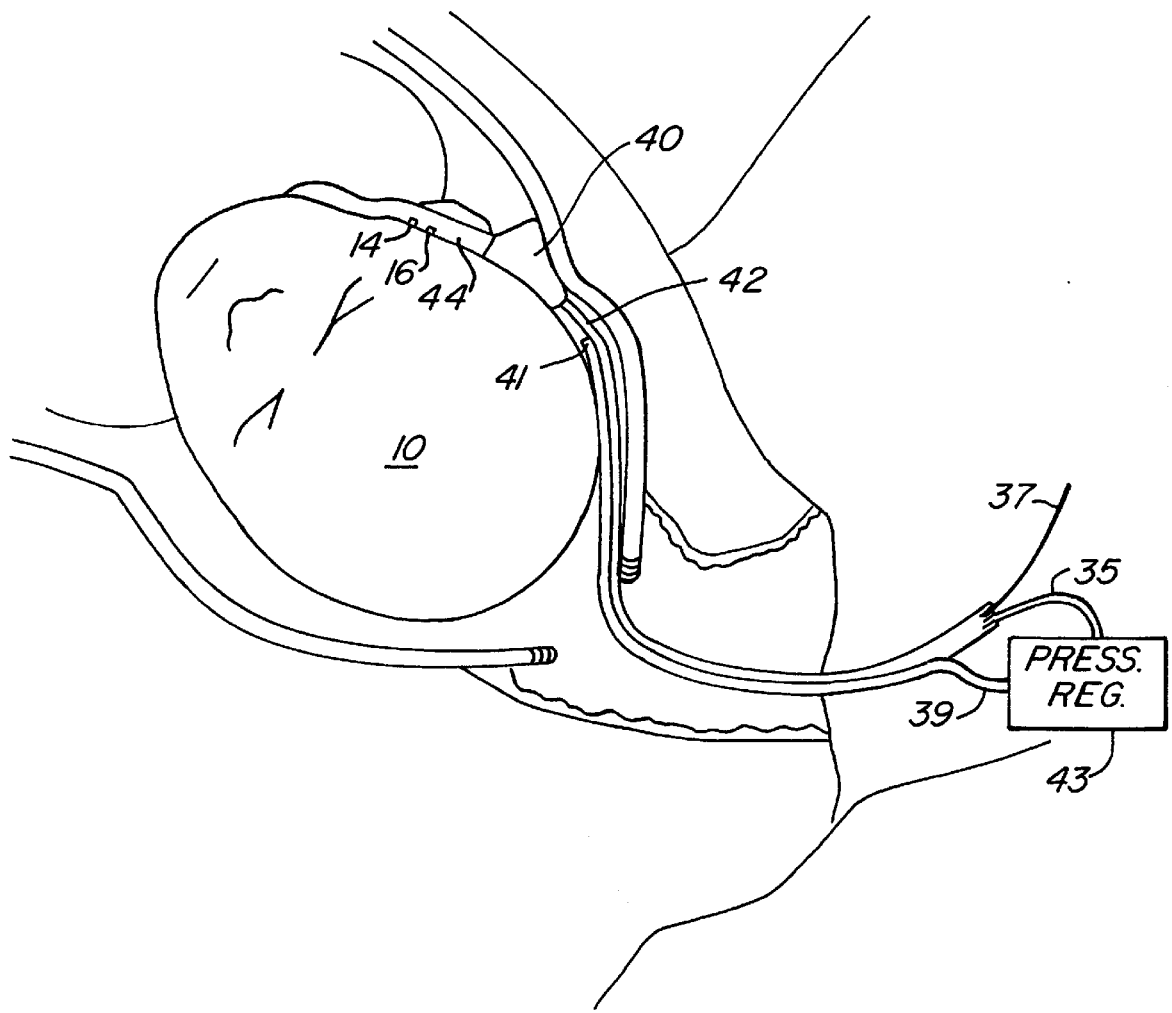
FIG. 3 is a diagram of a balloon attached to the cable jacket of a sensor.

FIG. 3 shows yet another alternate embodiment of the invention in which a balloon 40 is attached to a trailing edge of the sensor, proximal to the optics, on the jacket of a cable 42. Here, the sensor body 44 extends beyond the balloon 40, with the emitter 14 and detector 16 being positioned beyond where the balloon applies direct pressure to the fetus' head.

The balloon is filled with fluid, such as saline solution to a fixed volume, preferably to a fixed pressure relative to the amniotic pressure. By utilizing a fixed pressure relative to the amniotic pressure, the force holding the sensor against the fetus' skin is more constant and stable during motion (such as contractions) than if the balloon were filled to a fixed volume. Filling to a fixed pressure thus results in more stable pulse oximetry readings. FIG. 3 illustrates one method for controlling the fixed pressure. A tube 35 inside the cable jacket connects to the balloon. Wires or fiber optics 37 connect to the emitter and detector (which could simply be the ends of the fiber optics). A separate tube 39 is open at end 41 to connect to the amniotic fluid. Tubes 39 and 41 are connected to a pressure regulator, which maintains a constant pressure differential. For example, it may be desirable to maintain a 60 mm Hg pressure differential.

Figure 4:
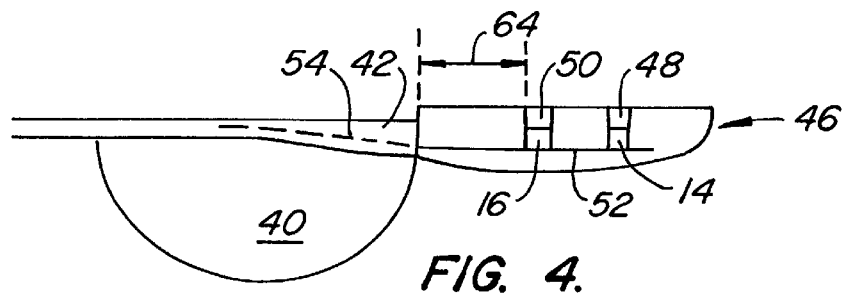
FIG. 4 is a more detailed diagram of a balloon attached to a cable jacket as in FIG. 3.

FIG. 4 illustrates the embodiment of FIG. 3 in more detail. A sensor housing 44 has a bevelled leading edge 46 to ease insertion into the uterus. Housing 44 can be made of a resilient material, such as Santoprene. The housing includes cavities into which emitter 14 and detector 16 are mounted. Preferably, the emitter and detector are covered with clear lenses 48 and 50, respectively. The emitter and detector are mounted on a substrate 52 containing the electrical connections, which connect to a cable 54 which is housed within a cable jacket 42. As can be seen, balloon 40 is attached to the cable jacket 42 at a position proximal to the detector 16. Preferably, a distance 64 between the edge of detector 16 and an edge of balloon 40 is at least ¼ inch, more preferably ½ inch, most preferably one inch.

Figure 5:
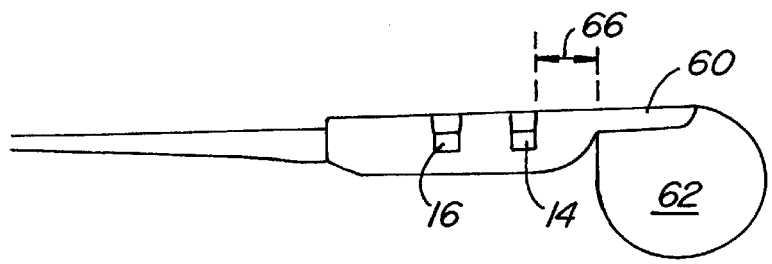
FIG. 5 is a more detailed drawing of one embodiment of a balloon attached to a leading edge of a sensor.

FIG. 5 shows an alternate embodiment in which the leading edge of the sensor housing is extended along a portion 60 with the balloon 62 being attached to leading edge 60. Thus, as can be seen, the balloon 62 is not directly behind and is separated from the emitter and detector. Leading edge 60 provides a somewhat stiff coupling to the remainder of the sensor housing, such that pressure forcing leading edge 60 against the fetus will also force the emitter and detector against the fetus. However, the major force is sustained by the leading edge portion 60, thus providing less force opposite the optics 14 and 16, and avoiding exsanguinating the tissue below the optics. Preferably, a distance 66 between the edge of emitter 14 and an edge of balloon 62 is at least ½ inch, more preferably ½ inch, most preferably one inch.

Figure 6:
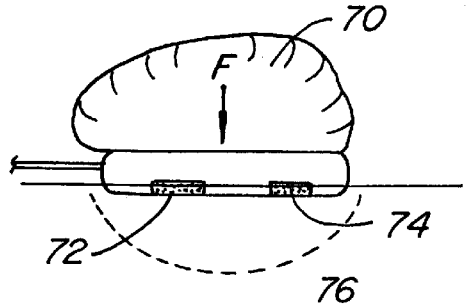
FIG. 6 is a diagram of a prior art balloon over both the emitter and the detector.
Figure 7:
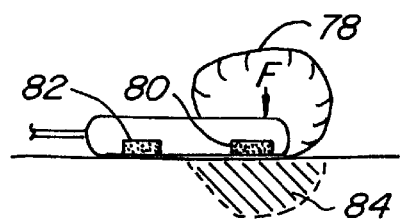
FIG. 7 is a diagram of an embodiment of the invention with the balloon over one of the emitter and detector.
Figure 8:
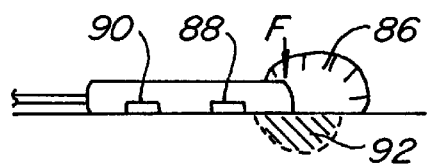
FIG. 8 is a diagram of an embodiment of the invention with the balloon over neither the emitter or detector.

FIG. 6 illustrates a fetal balloon sensor according to the prior art. A balloon 70 is over both emitter 72 and detector 74, causing an exsanguinated tissue region 76 beneath the emitter and detector. FIG. 7 illustrates one embodiment of the present invention wherein a balloon 78 is only over a detector 80, and not over an emitter 82. As can be seen, an exsanguinated region 84 only extends beneath detector 80, so that light passing from the emitter to the detector passes through some tissue that is not exsanguinated. In FIG. 8, the balloon 86 is not over either detector 88 or emitter 90, and an exsanguinated region 92 does not extend to the light path between the emitter and detector. In all 3 figures, F indicates where force is applied by the balloon to the sensor to hold the sensor against the fetus. Alternately, the positions of the emitter and detector could be reversed.

Figure 9:
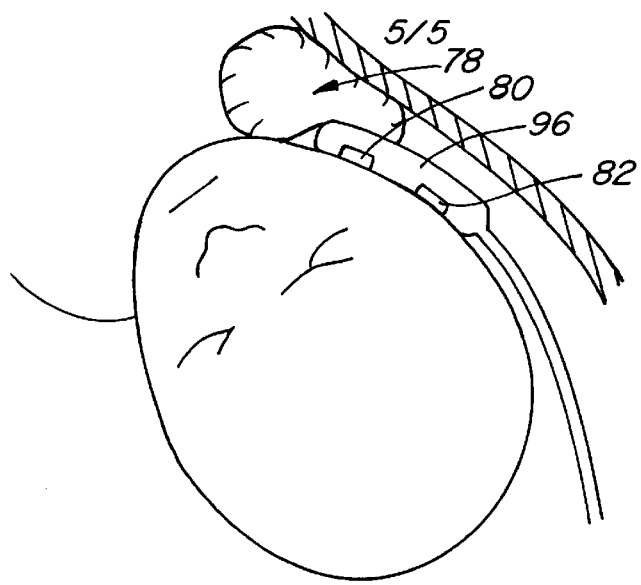
FIG. 9 is a diagram of the embodiment of FIG. 7 showing the sensor in place on a fetus.

FIG. 9 illustrates the sensor of FIG. 7 in place against a fetus 94, with sensor 96 being held in place by balloon 78.

Figure 10:
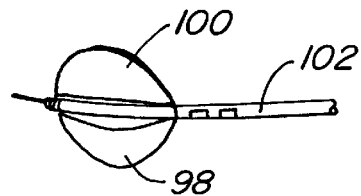
FIG. 10 is a diagram of an embodiment of the invention with balloons on the front and back of a sensor.
Figure 11:
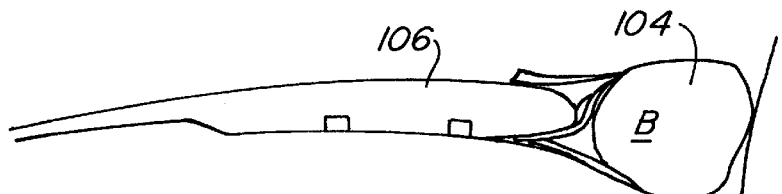
FIG. 11 is a diagram of an embodiment of the invention with a balloon attached to the front of a sensor.

FIGS. 10 and 11 illustrate alternate embodiments in which a balloon is attached to the side of the sensor facing the fetus. In FIG. 10, two balloons 98 and 100 on the bottom and top of the edge of sensor 102 are used. In FIG. 11, a balloon 104 on the bottom of sensor 106 uses the lower edge of the balloon to pull the sensor down against the fetus, rather than pushing it from the back of the sensor.

Figure 12:
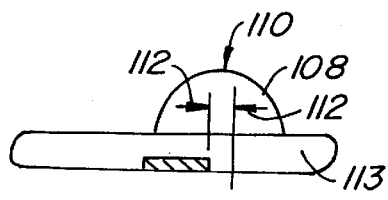
FIG. 12 is a diagram of a rounded balloon illustrating a limited contact region with a uterine wall.
Figure 13:
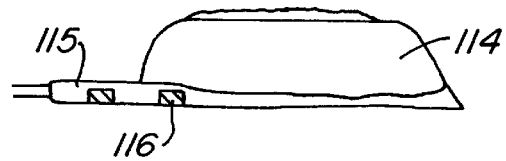
FIG. 13 is a diagram of a flattened balloon illustrating an extensive contact region with a uterine wall.

FIGS. 12 and 13 illustrate different balloon shapes for use with the invention. Balloon 108 of FIG. 12 is rounded, and will contact the uterine wall at a point 110, becoming slightly flattened so that the portion between lines 112 is in contact with the uterine wall, providing the greatest pressure to the portion of sensor 113 immediately below. In FIG. 13, a rectangular shaped balloon 114 is used, with the pressure from the uterine wall being more evenly spread because there is a larger contact area across most of the top of the balloon, thus distributing pressure away from detector (or emitter) 116 of sensor 115.

As will be understood by those of skill in the art, the present invention may be embodied in other specific forms without departing from the spirit or essential characteristics thereof. For example, a leading edge balloon could be attached by a cord to the sensor housing, and although not biasing the housing against the fetus, would provide an anchoring function. The function of the balloon to hold the sensor against the fetus could be accomplished by other means, such as a spring, sponge, self-inflating balloon, or other mechanisms. Accordingly, the foregoing description of the preferred embodiment is intended to be illustrative, but not limiting, of the scope of the invention which is set forth in the following claims.

What is claimed is:

1. An oximeter sensor comprising:

a sensor body;

a radiation emitter mounted in said sensor body;

a radiation detector mounted in said sensor body; and a balloon coupled to said sensor body at a location where no part of said balloon is opposite at least one of said emitter and; and wherein the radiation detector is used to detect radiation as a measure of oxygen saturation.

2. The sensor of claim 1 wherein said location is sufficiently remote so that a force on said sensor from said balloon does not directly press at least one of said emitter and said detector against a fetal tissue.

3. The sensor of claim 1 wherein said balloon extends distal to a leading edge of said sensor body.

4. The sensor of claim 1 wherein said balloon extends proximal to said sensor body.

5. The sensor of claim 4 further comprising a cable jacket to said sensor body, said expandable element being attached to said cable jacket.

6. The sensor of claim 1 wherein said sensor body has a leading edge extending distal to said radiation emitter and radiation detector and said balloon is attached to said leading edge.

7. The sensor of claim 1 wherein said radiation detector is removed from said balloon.

8. The sensor of claim 1 wherein said radiation emitter is removed from said balloon.

9. The sensor of claim 1 wherein said sensor is a pulse oximeter sensor.

10. The sensor of claim 2 wherein said sensor is a pulse oximeter sensor.

11. The sensor of claim 1 further comprising means for maintaining a constant pressure differential between a pressure exerted by said expandable element and an amniotic fluid.

12. The sensor of claim 13 wherein said expandable element is a balloon filled with a liquid, and said means for maintaining includes a pressure regulator.

13. An oximeter sensor comprising:

a sensor body;

a radiation emitter mounted in said sensor body;

a radiation detector mounted in said sensor body; and an expandable element coupled to said sensor body at a location where no part of said expandable element is opposite at least one of said emitter and said detector, said expandable element having an unexpanded relaxed state and an expandable non-relaxed state in a direction normal to said sensor body; and wherein said expandable element has a maximum expansion point for contacting a uterine wall, said maximum expansion point being at least one quarter inch from one of said emitter and said detector in a direction along a face of said sensor body.

14. An oximeter sensor comprising:

a sensor body;

a radiation emitter mounted in said sensor body;

a radiation detector mounted in said sensor body;

an expandable element coupled to said sensor body at a location where no part of said expandable element is opposite at least one of said emitter and said detector; and means adapted for communication with an amniotic fluid for maintaining a constant pressure differential between a pressure exerted by said expandable element and said; and wherein the radiation detector is used to detect radiation as a measure of oxygen saturation.

15. The sensor of claim 14 wherein said expandable element is a balloon filled with a liquid.

16. An oximeter sensor comprising:

a sensor body;

a radiation emitter mounted in said sensor body;

a radiation detector mounted in said sensor body;

a balloon filled with a liquid coupled to said sensor body at a location removed from at least one of said emitter and said detector; and means for maintaining a constant pressure differential between a pressure exerted by said balloon and an amniotic fluid, wherein said means for maintaining comprises a first tube coupled to said balloon;

a second tube adapted to be coupled to said amniotic fluid; and a pressure regulator coupled to said first and second tubes; and wherein the radiation detector is used to detect radiation as a measure of oxygen saturation.

17. An oximeter sensor comprising:

a sensor body;

a radiation emitter mounted in said sensor body;

a radiation detector mounted in said sensor body;

a balloon filled with a liquid coupled to said sensor body; and means for maintaining a constant pressure differential between a pressure exerted by said balloon and an amniotic fluid, wherein said means to maintaining comprises a first tube coupled to said balloon;

a second tube adapted to be coupled to said amniotic fluid; and a pressure regulator coupled to said first and second tubes; and wherein the radiation detector is used to detect radiation as a measure of oxygen saturation.

* * * * *

UNITED STATES PATENT AND TRADEMARK OFFICE
CERTIFICATE OF CORRECTION

PATENT NO. : 5,916,155
DATED : June 29, 1999
INVENTOR(S) : Levinson et al.

It is certified that error appears in the above-identified patent and that said Letters Patent is hereby corrected as shown below:

In claim 1, col. 5 at line 29, after the first occurrence of "and" insert --said detector--.

In claim 5, col. 5 at line 41, replace "expandable element" with --balloon--.

In claim 13, col. 6 at line 4, delete ";"after "body".

In claim 13, col. 6 at line 9, after "body" insert --and the radiation detector is used to detect radiation as a measure of oxygen saturation--.

In claim 14, col. 6 at line 21, after "said" insert --amniotic fluid--.

Signed and Sealed this

Thirtieth Day of November, 1999

Attest:

Q. TODD DICKINSON

Attesting Officer

Acting Commissioner of Patents and Trademarks